United States Patent [19]

Gude et al.

[11] Patent Number: 4,562,264

[45] Date of Patent: Dec. 31, 1985

[54] PROCESS FOR THE RECOVERY OF FIVE-MEMBERED RING DICARBOXYLIC ACID ANHYDRIDES

[75] Inventors: Fritz Gude, Herne; Ferdinand von Praun, Haltern, both of Fed. Rep. of Germany

[73] Assignee: Chemische Werke Huls Aktiengesellschaft, Marl, Fed. Rep. of Germany

[21] Appl. No.: 646,073

[22] Filed: Aug. 31, 1984

[51] Int. Cl.$^4$ .................. C07D 307/60; C07D 307/89
[52] U.S. Cl. ..................................... 549/261; 549/233; 549/247; 549/250; 549/251; 549/255; 549/262
[58] Field of Search .............. 549/233, 247, 248, 249, 549/250, 251, 255, 261, 262

[56] References Cited

U.S. PATENT DOCUMENTS 3,833,619  9/1974  Baumann et al. .................. 549/261
3,931,243  1/1976  Paustian et al. .................... 549/247

*Primary Examiner*—Richard L. Raymond
*Attorney, Agent, or Firm*—Oblon, Fisher, Spivak, McClelland & Maier

[57] ABSTRACT

A process for the recovery of five-membered ring dicarboxylic acid anhydrides from aqueous solutions of the corresponding dicarboxylic acids which entails (a) washing the aqueous solution of the dicarboxylic acid with a water-insoluble tertiary amine, and separating the resulting amine-acid salt from the water layer; and (b) adding an aromatic hydrocarbon entrainer for the water, removing the entrainer/water azeotrope by distillation and separating the five-membered ring dicarboxylic acid anhydride after phase separation; or adding an aliphatic hydrocarbon entrainer for the water, removing a ternary azeotropic mixture consisting of a hydrolytically stable anhydride, water and entrainer by distillation and separating the five-membered ring dicarboxylic acid anhydride after phase separation.

6 Claims, No Drawings

PROCESS FOR THE RECOVERY OF FIVE-MEMBERED RING DICARBOXYLIC ACID ANHYDRIDES

BACKGROUND OF THE INVENTION

1. Field of the Invention

The present invention relates to a process for the recovery of five-membered ring dicarboxylic acid anhydrides from aqueous solutions of the corresponding dicarboxylic acids.

2. Description of the Prior Art

After catalytic air oxidation of o-xylene or feedstocks containing o-xylene at about 400° C., the resulting phthalic anhydride is precipitated in the art by cooling of the reaction gas in a finned tube condenser. By scrubbing with water, practically all the organic substances are dissolved out of reaction gas, thus, the gas is largely freed from phthalic anhydride, whereby the anhydrides are hydrolyzed to carboxylic acids. The resulting aqueous solution is then treated, inter alia, with catalysts, e.g., thiourea and sulfur dioxide to rearrange the maleic acid obtained by degradation to slightly soluble fumaric acid. After its separation, the filtrate, according to the state of the art, is discharged as effluent. After pure o-xylene oxidation, the filtrate still contains 16 to 40 g/l of citraconic acid, 2 to 14 g/l of phthalic acid, 1 to 7 g/l of benzoic acid, 2 to 10 g/l of fumaric acid and small amounts of other substances.

For reasons relating to environmental protection and inasmuch as the effluent still contains an amount of valuable substances—especially citraconic acid—it would be extremely useful to attain a technically simple treatment process. After all, about 2 to 4 tons of citraconic acid are produced in the production of 1,000 tons of phthalic anhydride by oxidation of o-xylene.

Isolation of the acid by distilling off the water is not a plausible solution as it is far too expensive energetically and, hence, economically. Because of the volatility of the free citraconic acid with steam, alkali neutralization of the acid was previously necessary and, after evaporation, acidification was performed to be able to recover the mixture of free acid. DE-AS No. 15 93 246 describes another method. There citraconic anhydride is obtained from the aqueous solution of citraconic acid by azeotropic distillation of all the total water with benzene, toluene, chlorobenzene, dichloroethane, trichloroethane and/or hexane. DE-AS No. 15 93 546 proposes to distill off 80 to 90% of the solution water in vacuo at a bottom temperature below 80° C., then together with the water, to distill over the citraconic acid as anhydride at a bottom temperature over 80° C. and to separate the water to recover the oily, water-insoluble citraconic anhydride. Thus treatment of the aqueous citraconic acid solution by distilling off the water must be performed in a costly way with known processes. However, as an alternative, recovery of citraconic acid and the other acids contained in the fumaric acid effluent by extraction with suitable basic means should be theoretically possible. To be able to separate the water, the extracting agent and the salts from the extracting agent and carboxylic acid must be soluble in the water. A chemical reaction of the base with the acid should not be expected to occur.

M. I. Yakushkin (SU-PS No. 168 674) has reported the extraction of lower aliphatic monocarboxylic acids—such as formic, acetic, propionic and butyric acid—from aqueous solutions with trioctylamine. The water-insoluble acid salt was then isolated and heated to about 290° C., whereby the free acid was split off and recovered by distillation.

It was then found that dicarboxylic acids, such as maleic acid, citraconic acid, itaconic acid, phthalic acid, etc, could be extracted from aqueous solutions with tri-n-octylamine. Thus, for example, fumaric acid effluent can be subjected to solvent extraction with this base to remove all acidic contents. After separation of the oily water-soluble layer, a suitable aromatic hydrocarbon is mixed as entrainer for water. Upon heating, the entrainer and its water azeotrope distill over starting from about 130° C. Then, surprisingly, citraconic anhydride even at 105 to 110° C./15 mbar and phthalic anhydride in vacuo at about 160° C. can be separated by distillation, after some more benzoic acid had precipitated as an intermediate cut. By use of suitable aliphatic solvents, citraconic anhydride also in an heteroazeotropic mixture with the solvent and water can be stripped off from the effluent extract. After distillation, however, in both cases the amine in the bottom is partially decomposed.

The present inventors have found that, quite surprisingly, tertiary amines with branched primary aliphatic side chains in the 2-position, such as tri-(2-ethylhexyl)-amine, tri-(2-ethylbutyl)-amine, tri-(2-ethyldecyl)-amine, etc., have been found to be stable under the process conditions. All other reactions, including the extraction of the acids from the aqueous solution and the treatment of 1,2-dicarboxylic acids by distillation as anhydrides, can be performed with this class of substance as was done in the case of tri-n-octylamine. Unfortunately, however, in contrast with the more strongly basic, unbranched tertiary amines, complete extraction of the acid constituents of the fumaric acid effluent is not possible with these amines.

An advantage in using the above named branched amines is that the decomposition of the salts into their components under thermal load occurs at about 20° to 30° C. less than when the other tertiary amines are used. The release of the dicarboxylic acids occurring at lower temperatures is mild to the bases and increases the yield of recoverable anhydrides, if the subsequent distillation is performed at the lowest possible temperatures, and therefore, in a good technical vacuum.

An alternative milder method for treating the salt mixture can be effected, for example, by distilling off the citraconic anhydride under a vacuum, after distilling off the water/hydrocarbon azeotrope. Then an inert gas such as nitrogen, hydrogen, carbon monoxide, carbon dioxide, air, etc., is introduced at an elevated temperature under vacuum to the tertiary amine, whereby benzoic acid and phthalic anhydride are sublimated. When air is used, it is very advantageous to use tertiary amines with branched, aliphatic side groups in the 2-position, since this class of substances has unexpectedly proved itself to be considerably more stable to air oxidation than unbranched tertiary amines.

In a similar way, other five-membered ring dicarboxylic acid anhydrides, like the acids of the fumaric acid effluent, can be recovered from the aqueous solutions of their dicarboxylic acids. For example, succinic acid, itaconic acid and methylsuccinic acid can be so recovered as five-membered ring dicarboxylic acid anhydrides. However, the recovery of these five-membered ring compounds has been with very low yields and with inadequate purities.

Therefore, a need clearly exists for a process for recovering five-membered ring dicarboxylic acid anhydrides which provides excellent yields of the anhydrides.

SUMMARY OF THE INVENTION

Accordingly, it is an object of the present invention to provide a process for the recovery of five-membered ring dicarboxylic acid anhydrides which provides excellent yields of the anhydride.

It is also an object of this invention to provide a process for the recovery of five-membered ring dicarboxylic acid anhydrides with a very high purity.

According to the present invention, the foregoing and other objects are attained by providing a process for the recovery of five-membered ring dicarboxylic acid anhydrides from aqueous solutions of the corresponding dicarboxylic acids which entails washing the aqueous solution of the dicarboxylic acid with a water-insoluble tertiary amine and separating the resulting amine-acid salt from the water layer; and adding an aromatic hydrocarbon entrainer for the water and removing the entrainer/water azeotrope by distillation, and separating the five-membered ring dicarboxylic acid anhydride from the tertiary amine; or adding an aliphatic hydrocarbon entrainer for the water, removing the ternary azeotropic mixture consisting of hydrolytically-stable anhydride, water and entrainer, and separating the five-membered ring dicarboxylic acid anhydride from the tertiary amine.

DETAILED DESCRIPTION OF THE PREFERRED EMBODIMENTS

According to the present invention, it has now been found that a phase separation between the five-membered ring dicarboxylic acid anhydrides and the amines occurs above the melting point of the anhydrides, optionally after removal of the entrainer by distillation. For milder treatment, the anhydrides can then be purified by distillation after separation, while the amines can be recycled in the extraction process directly or after previous purification.

This invention therefore relates to a process for recovering five-membered ring dicarboxylic anhydrides from aqueous solutions of their dicarboxylic acids, wherein the aqueous solution is washed with water-insoluble tertiary amines, the resulting salt separated from the water, an entrainer, preferably aromatic, is added to the water and, after distilling off the entrainer/water azeotrope, the resulting five-membered ring dicarboxylic acid anhydrides are separated from the tertiary amine in vacuo.

The five-membered ring dicarboxylic acid anhydrides recovered according to the present invention can be based upon a variety of corresponding dicarboxylic acids. For example, the corresponding acids can be maleic acid, citraconic acid, itaconic acid, phthalic acid, succinic acid and methylsuccinic acid.

In the case of recovery of citraconic anhydride, because of its relatively high hydrolytic stability, it is also possible to proceed in such a manner that after extraction of the citracnic acid with the tertiary amine with addition of aliphatic hydrocarbons, for example, dodecane, as entrainer, a separation from the amine by distillation occurs. In this way, a ternary azeotrope—consisting of citraconic anhydride, dehydration water and entrainer—distills over. After phase separation, the citraconic anhydride can be separated.

If it is desired to separate exclusively citraconic acid from the fumaric acid effluent, then a washing with the above mentioned, slightly basic tertiary amines with branched primary aliphatic side chains in the 2-position can be used. By giving up a complete recovery, it is possible in this way to obtain almost pure citraconic acid which is present in the fumaric acid effluent. The remainder is discharged with the other acids as effluent.

A work published by D. Rittenberg and L. Ponticorvo in the Proceedings of the National Academy of Sciences (USA) 46 (1960), pages 822 to 824, states that many cyclic aliphatic anhydrides, inter alia, also citraconic anhydride, react during treatment with catalytic amounts of tertiary amines to form carbon dioxide. This reaction occurs in a disturbing way in the process according to the invention only if the treatment of the amine extract occurs with too high and too long a heat load.

The decomposition reaction is also greatly repressed if, instead of the catalytic amounts of tertiary amines, the amount of about 1 mole of tertiary amine and more per mole of dicarboxylic acid necessary for achieving good extraction results are used.

The present invention will now be further illustrated by certain examples and references which are provided for purpose of illustration only and not intended to limit the present invention.

EXAMPLE 1

1 liter of effluent from fumaric acid production, which contained 27.9 g (0.21 mol) of citraconic acid, 1.7 g of phthalic acid, 1.1 g of benzoic acid, 2.3 g of fumaric acid and smaller amounts of other substances, was twice extracted by absorptive precipitation for 15 minutes with 177 g (0.5 mol) of tri-n-octylamine each time and in this way almost completely deacidified. The amine extract was then introduced drop by drop at a pressure of 200 mbar in 1500 ml of dodecane heated to 160° to 165° C. and at the same time a distillate was drawn off, which separated in the receiver into an upper dodecane, a middle water and a lower citraconic anhydride phase. The citraconic anhydride yield amounted to 21.1 g, corresponding to 87.8% of theory.

The solvent-free bottom product from the above distillation was kept under enhanced vacuum at 150° to 160° C. and benzoic acid and the phthalic anhydride were stripped off with a nitrogen stream. The tri-n-octylamine, remaining as residue in the still, partially decomposed in this procedure.

EXAMPLE 2

1 liter of the effluent from example 1 was extracted by absorptive precipitation with 177 g (0.5 mol) each of tri-(2-ethylhexyl)-amine each time for 15 minutes. The resulting amine extract, which contained 69% citraconic acid, was then introduced drop by drop at a pressure of 200 mbar in 1500 ml of dodecane heated to 160° to 165° C. A heterozeotropic mixture simultaneously distilled off, which separated in the receiver into an upper dodecane, a middle water and a lower citraconic anhydride phase. The anhydride yield amounted to 15.4 g, corresponding to 93% of theory.

From the bottom product of the above distillation, benzoic and then phthalic anhydride were removed with a nitrogen stream under an enhanced vacuum at 150° to 160° C. The remaining tri-(2-ethylhexyl)-amine was almost free of degradation products and could be reused without purification.

EXAMPLE 3

An amine extract, which basically contained 141 g (0.4 mol) of tri-n-octylamine and 26 g (0.2 mol) of citraconic acid, was heated to boiling (145° C.) after addition of 250 ml of xylene and the amount of water resulting from anhydride formation was separated. Then the xylene was removed by distillation; the bottom product separated at room temperature into an upper amine and a lower anhydride phase. After distillation, the latter yielded 10.9 g of citraconic anhydride corresponding to 48.6% of theory. In addition, 1.4 g (6.2%) of anhydride was still dissolved in the dark colored amine phase. Amine loss amounted to 9.2%.

EXAMPLE 4

An amine extract consisting of 141 g (0.4 mol) of tri-(2-ethylhexyl)-amine and 26 g (0.2 mol) of citraconic acid, after addition of 250 ml of xylene, was heated to boiling at a pressure of about 450 mbar and a temperature of 110° to 115° C. The amount of water formed during anhydride formation was spun out and then the solvent was distilled off. The bottom product separated at room temperature into an upper amine and a lower anhydride phase. After distillation, the latter yielded 16.3 g of citraconic anhydride, corresponding to 72.8% of theory. The only slightly colored amine phase still contained 1.4 g (6.2%) of anhydride; it could be reused without further purification. The amine loss amounted to 0.96%.

EXAMPLE 5

An amine extract consisting of 54 g (0.15 mol) of tri-n-octylamine and 10 g (0.08 mol) of citraconic acid, after addition of 100 ml of octane, was heated to boiling (128° C.). The amount of water forming during anhydride formation was separated as a heteroazeotropic mixture with solvent and a little anhydride and the latter was isolated in an amount of 0.5 g, corresponding to 5.8% of theory. The bottom product separated into two phases after cooling to room temperature; the upper dark colored amine phase contained 0.94 (10.9% of theory) of citraconic anhydride, while 4.3 g (49.6% of theory) of the anhydride was able to be recovered from the lower phase by distillation. The amine loss amounted to 7.6%.

EXAMPLE 6

An amine extract consisting of 141 g (0.4 mol) of tri-(2-ethylhexyl)-amine and 16 g (0.2 mol) of citraconic acid, after addition of 250 ml of octane at 110° C. and under a low vacuum was heated to boiling. The amount of water formed during anhydride formation was separated as a heteroazeotropic mixture with solvent and a little anhydride and the latter was isolated in an amount of 2.0 g, corresponding to 8.9% of theory. After cooling to room temperature, the bottom product separated into an upper phase containing amine, which still contained 1.4 g (6.2% of theory) of anhydride, and in a lower phase, from which 17.7 g of citraconic anhydride (78.8% of theory) was able to be recovered by distillation.

The amine phase containing octane could be reused without further purification. The amine loss amounted to 0.7%.

EXAMPLE 7

2 liters of the effluent of example 1 was extracted with 353 g (1 mol) of tri-(2-ethylhexyl)-amine for 15 minutes by absorptive precipitation. With the resulting extract, which contained 3.5% citraconic acid, 2 liters of fresh effluent was extracted one more time, whereby the citraconic acid content in the extract rose to 6.3%. A similar third extraction yielded a further rise to 10.6% of citraconic acid in the extract. The total extraction rate after the three process steps was 27.9%. The processing of the extract can be performed according to the above examples. A corresponding enrichment in citraconic acid is not attained by use of tri-n-octylamine as the extracting agent.

Having now fully described this invention, it will be apparent to one of ordinary skill in the art that many changes and modifications can be made thereto without departing from the spirit or scope of the invention as set forth herein.

What is claimed as new and intended to be secured by Letters Patent is:

1. A process for the recovery of five-membered ring dicarboxylic acid anhydrides from aqueous solutions of the corresponding dicarboxylic acids which comprises:
    (a) washing the aqueous solution of the dicarboxylic acid with a water-insoluble tertiary amine having a branched aliphatic side chain in the 2-position, and separating the resulting amine-acid salt from the water layer; and
    (b) adding an aromatic hydrocarbon entrainer for the water, removing the entrainer/water azeotrope by distillation and separating the five-membered ring dicarboxylic acid anhydride after phase separation; or
    adding an aliphatic hydrocarbon entrainer for the water, removing a ternary azeotropic mixture consisting of a hydrolytically stable anhydride, water and entrainer by distillation and separating the five-membered ring dicarboxylic acid anhydride after phase separation.

2. The process according to claim 1, wherein said dicarboxylic acid is selected from the group of maleic acid, citraconic acid, itaconic acid, phthalic acid, succinic acid and methylsuccinic acid.

3. The process according to claim 1, wherein said tertiary amine is selected from the group of tri-(2-ethylhexyl)-amine, tri-(2-ethylbutyl)-amine, and tri-(2-ethyldecyl)-amine.

4. The process according to claim 1, wherein about one mole of tertiary amine or more is used per mole of dicarboxylic acid.

5. The process according to claim 2, wherein said dicarboxylic acid is citraconic acid.

6. The process according to claim 3, wherein said tertiary amine is tri-(2-ethylhexyl)-amine.

* * * * *